United States Patent [19]

Keeley

[11] 4,309,543

[45] Jan. 5, 1982

[54] PROCESS FOR PREPARING CYCLIC AMIDES

[75] Inventor: Donald E. Keeley, Delmar, N.Y.

[73] Assignee: Dynapol, Palo Alto, Calif.

[21] Appl. No.: 130,667

[22] Filed: Mar. 17, 1980

[51] Int. Cl.$^3$ .......................................... C07D 221/18
[52] U.S. Cl. ...................................... 546/76; 546/66; 546/98; 546/157
[58] Field of Search ...................... 546/76, 66, 98, 157

[56] References Cited

U.S. PATENT DOCUMENTS 4,132,713  1/1979  Broadhurst ................ 260/326.5 FL
4,206,240  6/1980  Bunes ..................................... 546/76

*Primary Examiner*—Paul M. Coughlan, Jr.
*Attorney, Agent, or Firm*—William H. Benz

[57] ABSTRACT

A process for preparing cyclic amides from an optionally substituted acetic acid and an aromatic aminocarbonyl compound is disclosed. The process employs a promoter comprising tetravalent titanium or silicon and a pyridine compound to effect formation of the cyclic amides.

10 Claims, No Drawings

PROCESS FOR PREPARING CYCLIC AMIDES

BACKGROUND OF THE INVENTION

1. Field of the Invention

This invention concerns a process for preparing cyclic amides. More particularly, it relates to a process for preparing cyclic amides from acetic acids and aromatic aminocarbonyl compounds.

2. The Prior Art

Cyclic amide groups appear throughout the range of organic chemistry. They may be found, for example, in monomers, in pharmaceuticals, and in a large number of synthetic and natural organic dyes and colorants. Previous methods for forming cyclic amides have included the method shown by Bunes in Belgian Pat. No. 861,945 wherein an aminoketone is reacted with a substituted acetyl chloride to give an uncyclized amide which is thereafter cyclized with base. Otteson et al, in U.S. Pat. No. 4,096,134, show the preparation of cyclic amides by the reaction of an aminoketone, i.e., a 1-aminoanthraquinone, with ethylacetoacetate in nitrobenzene. These are but two recent disclosures of representative routes. Other preparative routes to cyclic amides include the condensation of a 1-aminoanthraquinone with acetic anhydride with acid and nitrobenzene as shown by Lodge in U.S. Pat. No. 2,300,453, and the condensation of 1-aminoanthraquinone with benzoylacetic acid esters in the presence of base as shown by Peter et al, in U.S. Pat. No. 2,644,821. While all of these references produce cyclic amides, often their yields are low. This can be a serious shortcoming since the feed materials used, especially in the production of dyes or pharmaceuticals, are often complex and any yield loss can be quite costly. The process of this invention has as an advantage the achievement of very high yields of desired cyclic amide products. It has an additional advantage of proceeding facilely even at low to moderate temperatures, thus enabling the cyclic amide-functionality to be selectively introduced into molecules having other reactive groups.

As will be shown in more detail, the present process employs a promoter composed of titanium or silicon in a plus four valence state and pyridine. Some combinations of Ti(IV) and pyridine are shown in the art; e.g., *Naturwischeschaften*, 46, 446-7 (1959), in an article by G. S. Rao, shows $TiI_4 \cdot 2$ pyridine and $TiF_4 \cdot 2$ pyridine as complexes; the chloro equivalent is known, as well. It does not appear that these titanium complexes have been used as promoters for cyclic amide formation. To our knowledge, the closest reference concerning titanium may be found in the *Canadian Journal of Chemistry*, Vol. 48, pages 983-6, wherein $TiCl_4$ plus alkylamines were used in the formation of noncyclic carboxamides. The presently employed pyridine complexes are not shown nor are cyclic amides produced in this reference.

3. Statement of the Invention

It has now been discovered that tetravalent titanium or silicon, [Ti(IV) or Si(IV)], in combination with pyridine or a substituted pyridine, is an effective agent for promoting the selective formation of cyclic amides from substituted or unsubstituted acetic acid, and an aromatic aminocarbonyl compound. This process enables the preparation of cyclic amides in high yield and in some cases permits the facile preparation of cyclic amides not previously preparable or preparable only with great difficulty.

DETAILED DESCRIPTION OF THE INVENTION

In accord with this invention, acetic acid or a substituted acetic acid represented structurally as

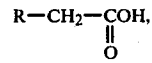

is reacted with an aromatic amino carbonyl, represented structurally as

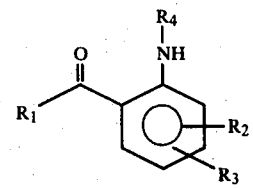

in the presence of a promoter composed of titanium (IV) or silicon (IV) and pyridine to give a cyclic amide of the formula

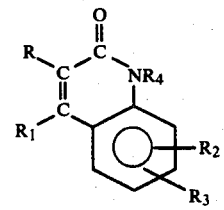

wherein R, $R_1$, $R_2$, $R_3$ and $R_4$ are organic molecular constituents. In this detailed description, the promoter system, the reactants and the reaction conditions will be separately discussed.

The Promoter System

The promoter employed in this process is Si (IV) or Ti (IV) and an optionally substituted pyridine compound. The silicon (IV) or titanium (IV) may be supplied in the form of one or more Si (IV) or Ti (IV) compounds such as the tetrahalides $SiF_4$, $SiCl_4$, $SiBr_4$, $SiI_4$, $TiF_4$, $TiCl_4$, $TiBr_4$ and $TiI_4$; the nitrates, $Si(NO_3)_4$ and $Ti(NO_3)_4$; the sulfates, $Si(SO_4)_2$ and $Ti(SO_4)_2$, as well as salts of organic acids such as the oxalate, lactate, acetate, propionate or the like. Of these, the halides are preferred, with the tetrachloride being a most preferred source of Si (IV) and Ti (IV). Although both silicon and titanium (IV) and mixtures thereof effectively promote the desired reaction, Ti (IV) is the preferred promoter metal species.

While not known with certainty, it appears, from observation of changes in the color of the reaction mixture, that the Si (IV) and Ti (IV) compounds undergo a transformation in situ in the reaction zone in contact with the reactants and other feedstocks to a Si (IV) or Ti (IV) ligand complex such as, for example, in the case of $TiCl_4$ and pyridine (pyr), a $TiCl_4 \cdot 2$ pyr complex. This suggests that one could use, as a source of Si (IV) or Ti (IV), such a complex or its equivalent. It is this complex of Si (IV) or Ti (IV) or an analog thereof that appears to be the actual active promoter.

It is therefore considered to be within the purview of this invention to employ as promoter any form of silicon and/or preferably titanium which, upon exposure to the conditions and reactants of this reaction, gives rise to an active Si (IV) or Ti (IV) complex. The above-identified titanium tetrahalides, especially TiCl$_4$, are set forth as preferred because of their ready availability and their ability to clearly promote the cyclic amide-forming reaction.

The promoter, as set forth above, is generally soluble in the reaction medium. It is considered, however, that a slurry of solid Si (IV) or Ti (IV):pyridine complex or Si (IV) or Ti (IV):pyridine complex deposited on a solid support such as charcoal or an inert oxidic support of high surface area, or a solid catalyst based on a suitably activated silica or titania support and pyridine might also be used.

The second component of the catalyst is pyridine or a substituted pyridine. Such compounds are defined structurally as

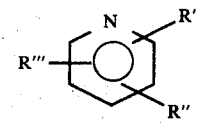

wherein R', R" and R'" independently are selected from hydrogen, lower alkyls of from 1 to 5 carbon atoms, aryls of 6 carbon atoms, alkaryls of 7–10 atoms or, in another suitable embodiment, R' and R" can be fused into another aromatic ring yielding a quinoline structure. Examples of these pyridines thus include pyridine, the methyl pyridines, 2-, 3- and 4-picoline; the dimethyl pyridines, 2,5-lutidine, 2,6-lutidine, 3,4-lutidine, and 3,5-lutidine; as well as the ethyl, propyl, butyl and pentyl equivalents and mixed alkyl equivalents; 2-, 3- and 4-benzyl pyridines; the 2-, 3- or 4-phenylpyridines, quinoline, isoquinoline, collidine and the like. These materials are well known to the art. Many are commercially available, such as from the Reilly Tar and Chemical Corporation. Of these materials, materials where at least one of R' and R" is hydrogen are preferred with pyridine itself being the most preferred, for reasons of ready availability.

The relationship of the amounts of the pyridine compound and Si (IV) and/or Ti (IV) is preferably controlled so that there is at least two moles of the pyridine compound per mole of total Si (IV) and/or Ti (IV) present. No upper limit on the pyridine compound needs to be set as the reaction proceeds with large excesses of the pyridine compound even to the point of said compound being used as the medium for the reaction. Generally, from about 2 moles to about 25 moles of the pyridine compound are employed per mole of silicon and/or titanium.

The Acetic Acid Reactant

The acetic acid reactant has the formula

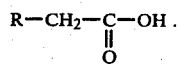

R may be hydrogen. R may also be an alkyl of from 1 to about 15 carbons, either linear or branched, saturated or unsaturated such that the "substituted acetic acid" is propionic through hexadecanoic acid or cyclohexylacetic acid or 3-hexeneoic acid or the like. R also may be an aryl or alkaryl or aralkyl of from 6 to about 20 carbons so as to give rise to substituted acetic acids such as phenylacetic acid, methylphenylacetic acid, benzylacetic acid, or the like. The "substituted acetic acids" may range from these simple materials through very complex molecules such as prostaglandins and the like. There is one limitation, however. The acetic acids must be unsubstituted or monosubstituted, that is, they must have at least two hydrogens on the carbon adjacent to the carbonyl group, as two of these hydrogens are needed for reaction. Any of the aforementioned R groups may additionally be substituted with halos, oxygen groups, hydroxyl groups or the like, that is, they may be optionally substituted.

In general, acetic acid, phenylacetic acid and 1 to 6 carbon alkyl-substituted acetic acids are preferred with phenylacetic acid being a most preferred acetic acid reactant.

The Aromatic Aminocarbonyl Reactant

The aromatic aminocarbonyl reactant has the formula

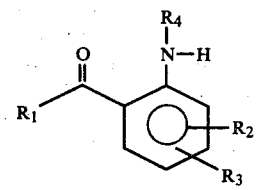

wherein R$_1$ through R$_4$ are organic molecular constituents.

The aminocarbonyl reactant is based on an aromatic ring to which is attached an amino group and ortho thereto a carbonyl group. The amine group can be a primary amine or can carry a single alkyl substituent of from 1 to about 8 carbons such as methyl, ethyl, the propyls, the butyls, the pentyls, the hexyls and the like or an aryl, alkaryl or aralkyl of from 6 to 10 carbons. This hydrogen, alkyl or aromatic substituent is shown as R$_4$ in the various structural formulae. The carbonyl can be present as an aldehyde or ketone group. Thus R$_1$ in the formula may be hydrogen or an alkyl chain such as with from 1 to 10 carbons. This chain can itself attach to the aromatic ring in a second position, thereby forming a cycloaliphatic ring. The carbonyl alkyl chain can itself be substituted with aliphatic and all of these groups can be substituted with heteroatom groups such as halos, sulfonyls, sulfonates, phosphonate, ethers, cyanos, nitros, alkoxys, and the like. The amine-containing aromatic ring itself may be substituted with up to two additional substituents, shown as R$_2$ and R$_3$ in the formulae. These may be hydrogen or lower alkyls of from 1 to 10 carbon atoms, fused or pendant aryls, cycloalkyls or alkaryls or the like, all of which may carry heteroatom substituents such as halos, sulfonyls, sulfonates, cyanos, or alkoxys.

Representative specific embodiments of the aromatic aminocarbonyl reactants in order of increasing complexity include the classes of materials given in Table I.

TABLE I

REPRESENTATIVE AMINOCARBONYL REACTANTS

| CLASS OF AMINOCARBONYL | REPRESENTATIVE STRUCTURE |
|---|---|
| 2-Acylanilines | [structure: benzene ring with NH-$R_4$ and C(=O)-$R_1$ ortho substituents] |
| 2-Aminobenzophenones | [structure: benzene ring with NH-$R_4$ and C(=O)-phenyl ortho substituents] |
| Tetralones | [structure: tetralone with NH-$R_4$] |
| 1-Amino-9-fluoronones | [structure: fluorenone with NH-$R_4$] |
| 1-Amino anthrones | [structure: anthrone with NH-$R_4$] |
| 1-Amino anthraquinones | [structure: anthraquinone with NH-$R_4$] |
| 7-amino indanones | [structure: indanone with NH-$R_4$] |
| 2-aryl carbazoles | [structure: carbazole with H-N and C(=O)-$R_1$] |
| 1-amino xanthenones | [structure: xanthenone with NH-$R_4$] |

In the structures of Table I, $R_4$ and $R_1$ independently are hydrogen, a 1 to 8 carbon alkyl, or a 6 to 10 carbon aromatic. All of the aromatic and nonaromatic rings shown in Table I may be variously substituted with one or more alkyls of from 1 to about 8 carbons, aryls and the like. Additional suitable substituents may include heteroatom substituents which, because of their location or properties, do not interfere with the desired cyclic amine formation such as halos, sulfonyls, sulfonates, ethers, phosphonates, cyanos, nitros, alkoxys, and thioethers.

It must be understood that the acetic acid reactants and aminocarbonyl reactants herein shown are intended merely to be representative of useful materials and their disclosure is not to be interpreted as all inclusive of possible materials.

The Reaction Conditions

In the process of this invention, one mole of optionally substituted acetic acid reacts with one mole of aminocarbonyl. It is generally preferred to use a slight excess of the less expensive reactant to assure total utilization of the more expensive material. Large excesses of one or the other reactant may be employed, but are not seen to offer any real advantages. Preferably, the molar ratio of acetic acid to the aromatic aminocarbonyl is from 1:3 to 3:1 with ratios of from 1:1.5 to 1.5:1 being preferred and ratios of from 1:1.25 to 1.25:1 being more preferred.

The silicon (IV) or titanium (IV) pyridine component is referred to herein as a "promoter" rather than a "catalyst." Its role, from a mechanistic point of view, is not completely understood. What is known is that it must be present to permit the desired compounds to be formed. The silicon or titanium/pyridine component is present in substantial "effective promoting" amounts, amounts generally greater than usually thought of as "catalytic." Preferably, Ti or Si is present in an amount of at least 0.25 mole per mole of the limiting one of the two reactants. It has been found that in general the more Si (IV) or Ti (IV)·pyridine that is present, the easier and faster the reaction proceeds. Excellent results are obtained with from 0.33 to 10 moles of Si (IV) or Ti (IV) per mole of limiting reactant with amounts of from 0.5 to about 5 moles of Si (IV) or Ti (IV) per mole of limiting reactant being more preferred. Because of the ability of excesses of Si (IV) or Ti (IV) to enhance the amide formation reaction rate, it is especially advantageous to use substantial excesses when the reactants are likely to enter into competing side reactions.

It has been stated to be generally preferred to carry out this reaction in liquid phase. The reaction medium employed may be made up of either of two types of material or a mixture thereof. The first medium material is pyridine or a liquid substituted pyridine as hereinabove described. This material is also useful as a promoter component. The second medium material comprises one or more aprotic inert solvents having atmospheric boiling points between about 50° C. and about 250° C. such as aromatic, aliphatic or mixed hydrocarbons, for example benzene, toluene, ethylbenzene, xylene, pentane, hexane, cyclohexane, petroleum distillate fractions and the like. Mixtures of the two classes of media may be employed as well and are generally preferred. The exact choice of the reaction medium is not seen as critical to the successful practice of the invention, but preferably it is selected within the classes set forth above. The amount of reaction medium preferably gives a concentration of Ti (IV) or Si (IV) of from 5 to 50% by weight and preferably 10 to 30%.

Reaction time and temperature parameters behave as one would expect—high temperatures give a high reaction rate, low temperatures a slow rate. The reaction definitely proceeds at 0° C. and at 115° C. There is no reason to doubt that the reaction occurs at temperatures of from −25° C. up to 250° C. The higher temperatures in many cases require superatmospheric pressure to keep the reaction medium and the reactants in liquid form. Preferably, the temperature is from −10° C. to 200° C. with excellent results being obtained with temperatures of from 20° C. to about 125° C.

The times required depend upon the temperature, amount of catalyst and the nature of the reactants involved. As guidelines, one finds that at 115° C., with 3-4 moles of Si (IV) or Ti (IV) per mole of limiting reactant, the reaction converting the limiting reactant to cyclic amides can be complete in 15 minutes. At 0° C. with 2 moles of Si (IV) or Ti (IV) per mole of limiting reactant, the reaction may take up to 100 hours or more to complete. In general terms, and recognizing that only the higher temperatures and highest proportions of Si (IV) or Ti (IV) can produce good yields in the shorter time, and that exposure to stressful temperature conditions for long times can degrade desired products, times of from 3 minutes to 200 hours may be employed. Also, it is generally observed that Ti (IV) is more effective, with faster reactions, etc., than Si (IV). Times from 5 minutes to 4 hours are generally preferred with times from 10 minutes to 3 hours being most preferred.

In view of the fact that the concentration of amide product can be easily determined by HPLC analysis or the like, one would probably wish to tailor the reaction times to the other conditions employed, halting the reaction when the limiting reactant has been essentially completely consumed.

Other Process Steps

Recovery of the cyclic amide is effected by standard organic chemical recovery steps such as precipitation of the amide by chilling the reaction mixture or the addition of nonsolvents. The amide may also be extracted from the reaction mixture and thereafter recovered from the extract by crystallization, precipitation, or the like.

The recovered amide may be purified by recrystallization, extraction, washing or like processes known to the art, if desired.

The Amide Products and Their Uses

The present process finds diverse use preparing a wide range of valuable cyclic amides. Anthraquinone starting materials yield anthrapyridones which are useful as dyestuff components. See, for example, the use of anthrapyridones shown in Belgian Pat. No. 861,945 of Bunes or in U.S. Pat. No. 4,096,134, of Otteson et al. As well, prostaglandins and polymerizable cyclic amides may be formed. These materials have established utilities as dyestuffs, monomers, pharmaceuticals and pharmaceutical intermediates.

The process of this invention will be further described by the following examples and comparative experiments. These are presented to exemplify the invention. They are not to be construed as limiting the invention's scope.

EXAMPLE I

A mixture of 3.16 g (10 mmol) 1-amino-4-bromo-2-methyl anthraquinone (AMBAX), 1.36 g (10.0 mmol) phenylacetic acid, 950 mg (5.0 mmol) of titanium tetrachloride and 30 ml of pyridine was heated at reflux (115° C.) under argon. After 10 minutes, TLC analysis showed the presence of a new material. The reaction was continued overnight. The next morning no AMBAX starting material was found by TLC analysis and the new material was the sole product. This product was recovered by filtration in 90% yield (3.74 g) as green-yellow crystals. Analysis showed that the product was a cyclic amide of the formula

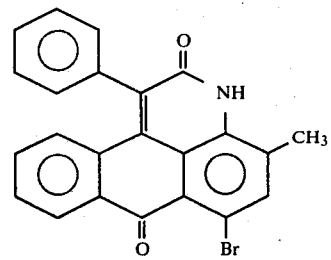

which material is useful as an intermediate in the formation of red colorants as shown by Bunes in Belgian Pat. No. 861,945.

EXAMPLE II

A series of 5 reactions was run to demonstrate the effect of varying the amount of titanium promoter employed. The materials and general methods employed were the same as used in Example I. AMBAX was held at 10 mmol in each reaction. Phenylacetic acid was maintained at 12 mmol in each reaction. Refluxing pyridine (25 ml) was the solvent. The amount of $TiCl_4$ promoter ranged from 0.5 equivalents (basis AMBAX) to 3.6 equivalents on the same basis. As shown in Table 1, it was observed that the reaction proceeded faster and to higher conversion as the amount of promoter was increased.

TABLE 1

| Reaction No. | Eq. of $TiCl_4$ | Conversion of AMBAX to Anthrapyridine (reaction time) |
|---|---|---|
| 2a | 0.5 | 50% (24 hrs) |
| 2b | 1.0 | 50% (24 hrs) |
| 2c | 1.5 | 90% (24 hrs) |
| 2d | 2.0 | 100% (2 hrs) |
| 2e | 3.6 | 100% (0.5 hrs) |

EXAMPLE III AND COMPARATIVE EXPERIMENTS

Eleven reactions were carried out which demonstrate the need for an optionally-substituted pyridine compound in conjunction with the titanium promoter. The reactions were carried out on several different scales—10 mmol, 20 mmol, etc., but followed the general proportions of reaction 2e. The results of these ten reactions are given in Table 2 and show that a pyridine compound is a necessary part of the titanium system.

TABLE 2

| Reaction No. | Solvent | Reaction Product |
|---|---|---|
| 1 (Example 1) | Pyridine | Cyclic Amide[1] |
| 3a | ⅓ toluene/pyridine | " |
| 3b | 1/1 toluene/pyridine | " |
| 3c | 3/1 toluene/pyridine | " |
| 3d | Toluene | Anthraquinone dimer[2] |
| 3e | 2/1 toluene/$NEt_3$ | No reaction |
| 3f | 8/1 toluene/methanol | " |
| 3g | Toluene/$NH_3$ (gas) | " |
| 3h | Toluene | " |
| 3i | DMF | " |
| 3j | $CHCl_3$ | " |

TABLE 2-continued

| Reaction No. | Solvent | Reaction Product |
|---|---|---|
| 3k | N,N-dimethylaniline | " |

[1] Product of Example 1.

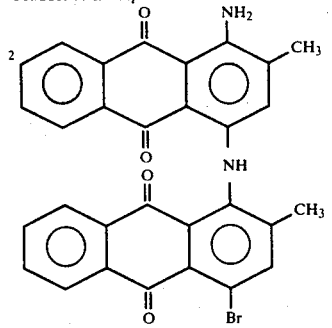

EXAMPLE IV

Reaction 2e of Example II is repeated seven times with substituted pyridines being serially substituted for all or part of the pyridine employed in that reaction. The same temperature is applied and all other conditions and amounts of that reaction are repeated.

| Reaction No. | Pyridine Component |
|---|---|
| 4a | 2-picoline |
| 4b | 3-picoline |
| 4c | 2,5-lutidine |
| 4d | 2,5 di-propylpyridine |
| 4e | quinoline |
| 4f | 3-benzylpyridine |
| 4g | collidine |

In each case, the cyclic amide reaction product of 2e is formed.

EXAMPLE V

The general preparation of reaction 2e was repeated varying the metal component of the promoter.

In reaction 7a, 6.9 mmol of SiCl$_4$ was substituted for the TiCl$_4$. The mixture was refluxed for 5 hours after which it was checked by TLC and found to have reacted essentially as in reaction 2e with about 50% conversion to the cyclic amide. Variation of promoter level as shown in Example II with SiCl$_4$ would be expected to produce the variation in conversion observed in Example II. Variation of the pyridine component and medium as shown in Examples II and IV would be expected to give the same results when Si (IV) is employed. Other sources of Ti (IV) and Si (IV) are employed in general reaction 2e. In place of TiCl$_4$, TiBr$_4$ and Ti(NO$_3$)$_4$ are employed. In place of SiCl$_4$, SiBr$_4$ is employed. All give results similar to those observed in reaction 2e.

EXAMPLE VI

Reaction 2e of Example II was repeated with a variety of different acetic acid reactants in place of phenylacetic acid. In reaction 6a acetic acid itself was employed as follows. A mixture of AMBAX (50.0 mmol), acetic acid (60.0 mmol), TiCl$_4$ (180 mmol) was stirred with 100 ml of pyridine and 100 ml of toluene. The mixture was heated to reflux for 4 hours. TLC analysis showed that no AMBAX remained and that a new compound had formed. The reaction mixture was cooled to about 60° C., 100 ml of methanol was added and the mixture cooled further to room temperature. A green solid was recovered, washed twice with methanol and air-dried. Analyses showed that it was the cyclic amide,

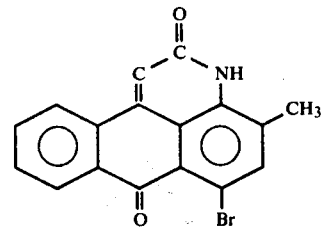

In reaction 6b, phenoxyacetic acid was employed. Into 100 ml of pyridine was added 19.8 ml of TiCl$_4$ (180 mmol) in 100 ml of toluene. AMBAX (50 mmol) and 60 mmol of phenoxyacetic acid were added and the mixture was refluxed for two hours. The mixture was checked by TLC and the conversion of all the AMBAX to a new compound was noted. The mixture was cooled to 60° C., 100 ml of methanol was added and the mixture further cooled to room temperature. A solid product was recovered, washed and dried. Upon analysis it was determined to be the cyclic amide

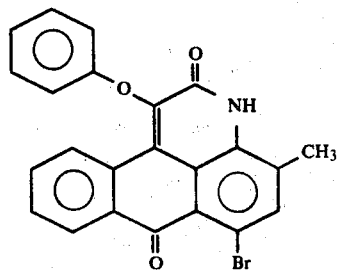

The reaction and general procedure of reaction 6a of this example could be employed with a range of additional acetic acids to yield additional anthrapyridones. The acid

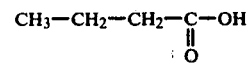

would yield the amide

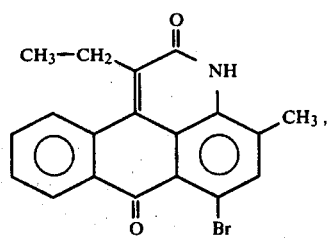

the acid

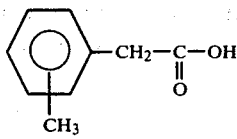

would yield the amide

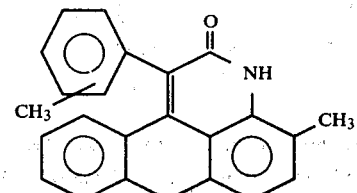

the acid

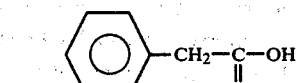

would give the product

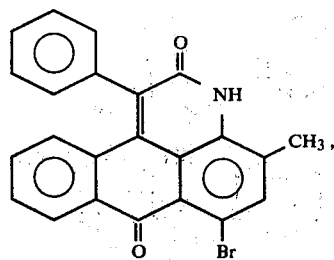

and the acid

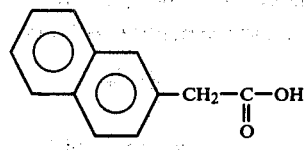

would give the product

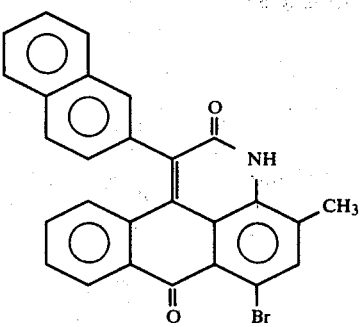

EXAMPLE VII

In this example, different aminocarbonyls are employed in place of AMBAX in the general reaction of Example II.

In experiment 7a, 20.2 g (50 mmol) of bromaminic acid,

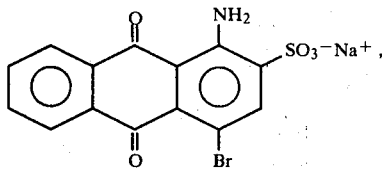

was added to a mixture of 200 ml of pyridine and 180 mmol of titanium tetrachloride and 60 mmol of phenylacetic acid. The mixture was heated to reflux for three hours, cooled, diluted with 80 ml of methanol and further cooled. An orange solid, determined to be the cyclic amide,

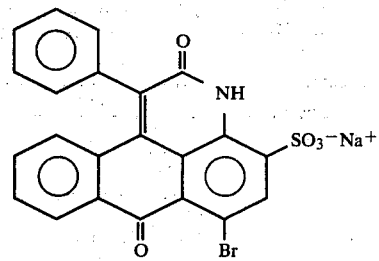

was recovered by filtration, washed and dried.

The foregoing reaction could be repeated substituting the following aminocarbonyl compounds.

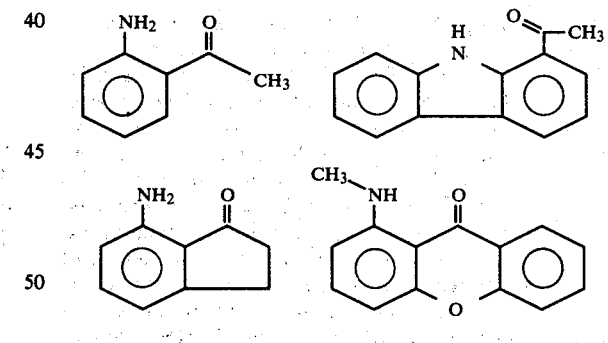

EXAMPLE VIII

The reaction 2e of Example II was repeated twice varying the scale and reaction temperature. In reaction 2e, at 115° C., the reaction was observed to proceed to completion within 30 minutes. In reaction 8a, a 4-neck, 2000 ml, round bottom flask, equipped with a mechanical stirrer, water condenser, argon bubbler, internal temperature probe and pressure equalizing dropping funnel, was charged with 900 ml of pyridine. Titanium tetrachloride was then added over a 10 minute period, during which time the internal temperature rose to approximately 85° C. When the reaction temperature had cooled to 60° C., AMBAX and phenylacetic acid were added and the reaction mixture heated at an internal temperature of 63°–65° C. for 2.5 hours. TLC analysis (silica gel/CHCl₃) indicated no AMBAX present, but there was cyclic amide present and a brown origin spot. The reaction mixture was allowed to cool to room temperature. The amide could be seen crystallizing on the sides of the reaction flask where pyridine was splashing. The reaction mixture was filtered and the collected solid washed with methanol (3×100 ml). The solid was dried in a vacuum oven at 60° C. and 0.2 mm for 16 hours. Yield: 77 g (75%).

In reaction 8b the materials and amounts of reaction 2e were used. Prior to adding the aromatic amine, the mixture was cooled to 0° C. and there maintained. After 15 minutes, a TLC analysis was carried out which clearly showed that the cyclic amide was forming, albeit slowly.

What is claimed is:

1. A process for the synthesis of a cyclic amide which comprises contacting acetic acid or a substituted acetic acid with an aromatic amino carbonyl compound of the formula

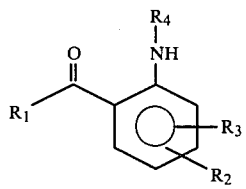

wherein $R_1$ is hydrogen or an optionally substituted 1 to 10 carbon atom alkyl chain, $R_2$ and $R_3$ independently are selected from alkaryls, hydrogens, 1 to 10 carbon alkyls, aryls, cycloalkyls and $R_4$ is selected from hydrogen, alkyls of from 1 to 8 carbons, and aryls, alkaryls and aralkyls of from 6 to 10 carbons, in the presence of a promoting amount of a metal selected from titanium (IV) and silicon (IV), and a pyridine compound under effective reaction conditions of a liquid phase reaction, acetic acid:amino carbonyl compound mole ratio of from 3:1 to 1:3, a reaction temperature of from −10° C. to 200° C. and a reaction time dependent upon the reaction temperature and selected in the range of from 3 minutes to 200 hours.

2. The process of claim 1 wherein said metal is titanium (IV).

3. The process of claim 1 wherein said metal is silicon (IV).

4. The process of claim 2 wherein said pyridine compound is pyridine.

5. The process of claim 3 wherein said pyridine compound is pyridine.

6. A process for the synthesis of a cyclic amide which comprises contacting in liquid phase an acetic acid of the formula

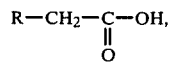

wherein R is an optionally substituted 1 to 15 carbon atom alkyl, or 6 to 20 carbon atom aryl or alkaryl with an aromatic aminocarbonyl compound of the formula

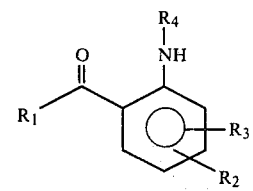

wherein $R_1$ is hydrogen or an optionally substituted 1 to 10 carbon atom alkyl chain, $R_2$ and $R_3$ independently are selected from arkaryls, hydrogens, 1 to 10 carbon alkyls, aryls cycloalkyls and $R_4$ is selected from hydrogen, alkyls of from 1 to 8 carbons, and aryls, alkaryls and aralkyls of from 6 to 10 carbons, under effective reaction conditions including acetic acid to amino carbonyl component mole ratio of 3:1 to 1:3, a temperature of from 20° C. to 125° C. and a reaction time of from 5 minutes to 4 hours with a promoting amount of a metal selected from titanium (IV) and silicon (IV) and a pyridine compound thereby forming a reaction product containing said cyclic amide and recovering said cyclic amide from said reaction product.

7. The process of claim 6 wherein said metal is titanium (IV).

8. The process of claim 7 wherein said pyridine compound is pyridine.

9. The process of claim 8 wherein the amount of titanium (IV) is at least about 0.25 moles per mole of the aminocarbonyl compound and the amount of pyridine is from 2 to 25 moles per mole of titanium (IV).

10. The process for preparing an anthrapyridone of the formula

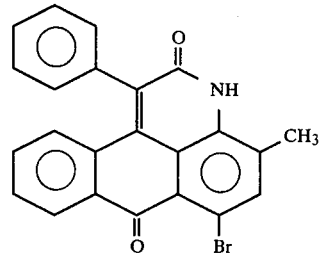

which comprises contacting phenyl acetic acid with 1-amino-4-bromo-2-methyl anthraquinone in essentially equimolar proportions with from 0.33 to 10 moles of titanium (IV) per mole of the anthraquinone, and from 2 to 25 moles of pyridine per mole of titanium (IV) in liquid phase at a temperature of from 20° C. to 125° C. for from 5 minutes to 4 hours, thereby forming a reaction product containing the anthrapyridone and thereafter recovering the anthrapyridone from said reaction product.

* * * * *